United States Patent [19]

Rosa et al.

[11] Patent Number: 4,503,707
[45] Date of Patent: Mar. 12, 1985

[54] HYGROMETRY PROBE

[75] Inventors: Eugene J. Rosa, Martinez; James B. Jerde, Scotts Valley, both of Calif.

[73] Assignee: Ondyne Inc., Concord, Calif.

[21] Appl. No.: 479,147

[22] Filed: Mar. 28, 1983

[51] Int. Cl.³ ............................................. G01W 1/02
[52] U.S. Cl. ................................... 73/336.5; 364/556
[58] Field of Search ............... 73/336, 336.5; 364/550, 364/556, 573

[56] References Cited

U.S. PATENT DOCUMENTS

| 3,075,385 | 1/1963 | Stover. | |
|---|---|---|---|
| 3,121,853 | 2/1964 | Jason et al. | |
| 3,523,244 | 8/1970 | Goodman et al. | |
| 3,539,917 | 11/1970 | Chleck. | |
| 3,987,676 | 10/1976 | Bennewitz. | |
| 4,319,485 | 3/1982 | Terada et al. | 73/336 |
| 4,379,406 | 4/1983 | Bennewitz et al. | 73/336.5 |

FOREIGN PATENT DOCUMENTS 443350 12/1975 U.S.S.R. .............................. 73/336.5

OTHER PUBLICATIONS

Kammermaier, J., et al., *Electronic Humidity Sensor with Linear Characteristic*, Siemens Comp., vol. XV, No. 1, pp. 22–26, Mar. 1980.

Whitehaus, G., *Linearizing Relative Humidity Measurements*, Instr. & Control Sys., pp. 72–73, Sep. 1972.

Primary Examiner—Gerald Goldberg
Assistant Examiner—Joseph W. Roskos
Attorney, Agent, or Firm—Barnes & Thornburg

[57] ABSTRACT

A probe has a housing which includes a moisture sensor for providing a non-linear moisture-related signal and a signal processor for linearizing the moisture-related signal and converting the signal to a digital output signal indicative of a moisture measurement. Temperature and pressure sensors are also included and provide a temperature-related signal and a pressure-related signal in the probe. The signal processor processes the moisture-related signal as a function of one or both of the temperature and pressure-related signals and provides another moisture-related output signal. The signal processor includes a serial data output for transmitting the digital moisture-related signal and digital temperature and pressure-related signals along a signal data transmission line.

21 Claims, 6 Drawing Figures

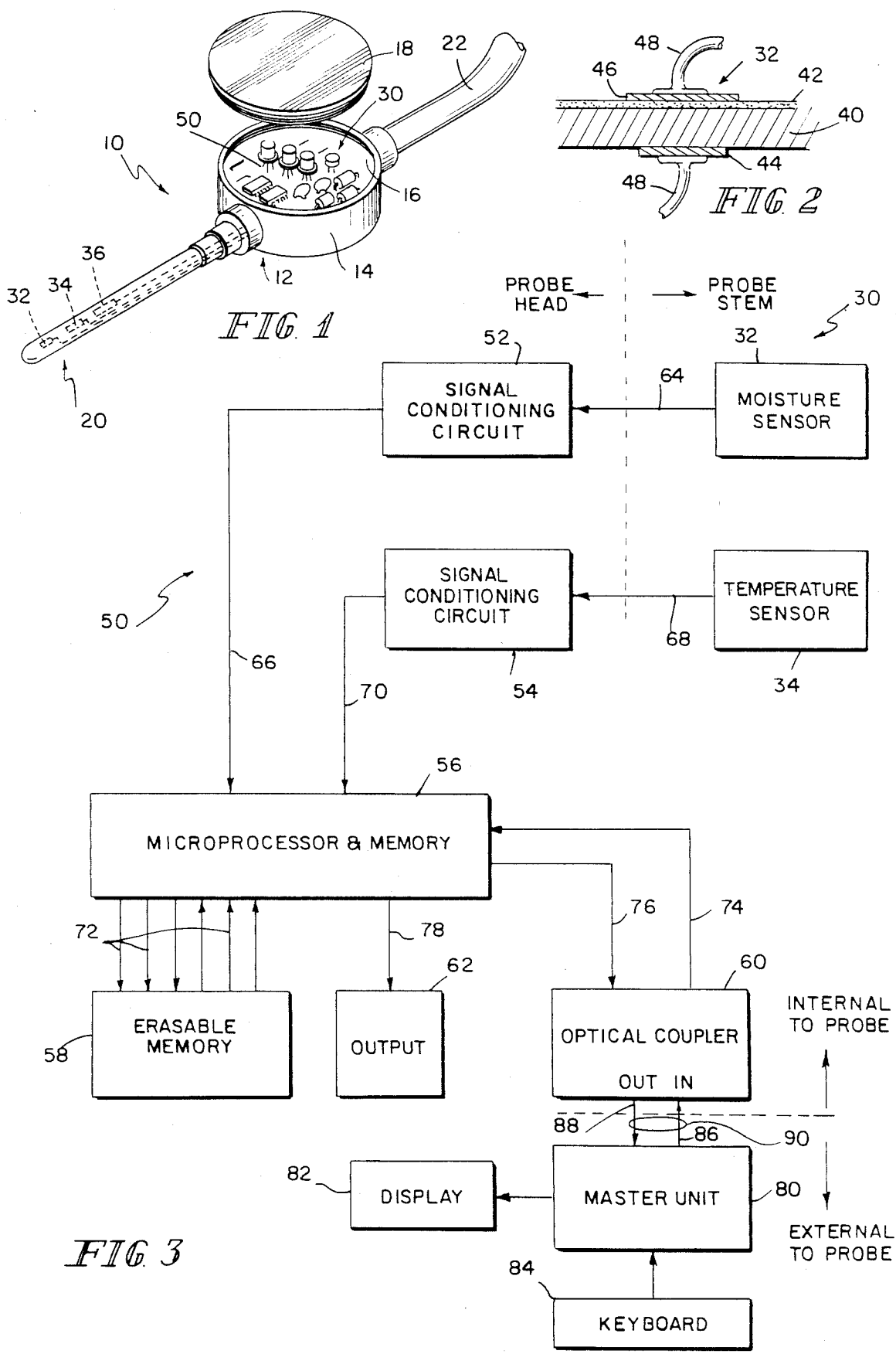

HYGROMETRY PROBE

This invention relates generally to devices for measuring physical conditions, and more specifically, to a temperature and pressure compensated hygrometry probe.

Aluminum oxide hygrometry probes or sensors are well known in the art. See, for example, the following U.S. Pat. Nos.: 3,075,385; 3,121,853; 3,523,244; 3,539,917; and 3,987,676. These sensors sense moisture using resistance and/or capacitance, and typically include a first electrically conductive layer of metal such as aluminum, a layer of hygrometric material such as aluminum oxide, and a second electrically conductive layer of metal formed over the aluminum oxide in the form of a sandwich. The second layer is sufficiently thin to allow moisture to pass therethrough to the hygrometric layer, causing changes in impedance between the first and second electrically conductive layers.

Aluminum oxide hygrometers are inherently non-linear. Thus, corrective steps must be taken to achieve an accurate measurement. As disclosed in U.S. Pat. No. 3,987,676, previous efforts have been made to produce an improved aluminum oxide sensor having a linear impedance variation with variations in moisture. However, most aluminum oxide sensors provide a non-linear analog output. Heretofore, it has been necessary to connect each probe to external auxiliary elements to linearize the probe output. Further, if the probe is used in connection with computer systems, the output must be converted from an analog signal to a digital signal. The use of multiple probes requires multiple external devices for linearizing and digitally converting each probe output.

It is desirable that each individual probe have its own linearization and analog-to-digital conversion capabilities so that it provides a linearized digital output signal. It is also desirable that the digital output signal be indicative of dew point, partial vapor pressure of water, temperature, and pressure, and that each of these values be transmitted through a common data link in a multiple probe system. In addition, it is sometimes desirable that the moisture measurement be processed as a function of temperature or pressure to provide different moisture output signals.

One object of the present invention is to provide a probe with internal linearization and analog-to-digital conversion capabilities.

In a hygrometry probe, it is an object of the present invention to provide a system for sensing moisture, temperature, and pressure, linearizing the moisture measurement, and providing a digital output signal indicative of the linearized moisture, temperature, and pressure measurements.

Another object of the present invention is to provide a hygrometry probe for sensing moisture and temperature and for producing a moisture-related output signal which is a function of the temperature.

Still another object of the present invention is to provide a hygrometry probe for sensing moisture, temperature, and pressure and for producing two moisture-related output signals which are functions of temperature and pressure.

A further object of the present invention is to provide a multiple hygrometry probe system for transmitting a plurality of measurement values from each probe over a common data link to a master monitoring point.

A hygrometry probe embodying the present invention includes a housing, sensing means in the housing for sensing moisture and providing a non-linear moisture-related signal, and signal-processing means in the housing for linearizing the non-linear moisture-related signal and providing a digital moisture-related signal.

The probe housing includes a head and a hollow stem or blade extending from the head. The moisture-sensing means is housed in the stem. The signal-processing means is housed in the head. The probe thus comprises a stand-alone unit with sensing means and signal-processing means integrated into the probe housing.

In one embodiment, the probe includes first sensing means for sensing moisture and providing a moisture-related signal, second sensing means for sensing temperature and providing a temperature-related signal, and signal-processing means for linearizing the moisture-related signal and converting the moisture-related signal and temperature-related signal to digital output signals.

According to an illustrative embodiment, the moisture-sensing includes a capacitive aluminum oxide sensor. The capacitance of the moisture sensor varies in relation to moisture. A first signal-conditioning means for coupling the moisture-sensing means to the signal-processing means includes an oscillator. The oscillator generates a square wave, the frequency of which is related to the capacitance of the moisture sensor. The temperature-sensing means includes a Zener referenced diode sensor. The temperature sensor provides a DC voltage, the level of which is related to the temperature. A second signal-conditioning means for coupling the temperature-sensing means to the signal-processing means includes a voltage-to-frequency converter. The voltage-to-frequency converter changes the voltage signal supplied by the temperature sensor to a square wave. The frequency of the square wave is related to the voltage level of the temperature sensor.

In the illustrative embodiment, the signal-processing means comprises a microprocessor. The microprocessor is programmed to continously read the moisture and temperature-related signals. Additionally, means for coupling the first and second signal-conditioning means to the microprocessor comprises a multiplexer. The square-wave moisture-related signal is coupled to one input of the multiplexer, and the square-wave temperature-related signal is coupled to another input of the multiplexer. The microprocessor is coupled to the multiplexer and selects which signal it wishes to read.

In a further illustrative embodiment, the probe also includes a third sensing means in the housing for sensing pressure and providing a press-related signal. The microprocessor converts the pressure-related signal to a digital output signal representative of pressure. This embodiment further includes means for coupling the temperature-sensing means and the pressure-sensing means to the second signal-conditioning means. This coupling means comprises another multiplexer.

The microprocessor includes means for generating a serial data output signal to send the linearized moisture value, temperature value, and pressure value to a master monitoring system. The microprocessor further includes means for selectively responding to a serial data input signal so that a plurality of probes can be coupled to one master monitoring system by a common link.

The microprocessor is programmed to compare the moisture value, temperature value, and pressure value against preset limits which have been entered by the user into an erasable memory unit. An output of the microprocessor is set or cleared based upon the result of the comparison. The output can be used to trigger alarms.

In a further embodiment of the present invention, the microprocessor processes the moisture-related signal as a function of temperature and pressure and provides additional digital moisture-related signals as functions of the temperature and pressure.

Various other features and advantages of the present invention will become apparent from the following description and the accompanying drawings which illustrate an embodiment of the invention. In the drawings:

FIG. 1 is a perspective view of a probe embodying the present invention;

FIG. 2 is a cross-sectional view of an aluminum oxide moisture sensor employed in the probe shown in FIG. 1;

FIG. 3 is a functional block diagram of one embodiment of a sensing and signal-processing system included in the probe shown in FIG. 1;

Figure 4:
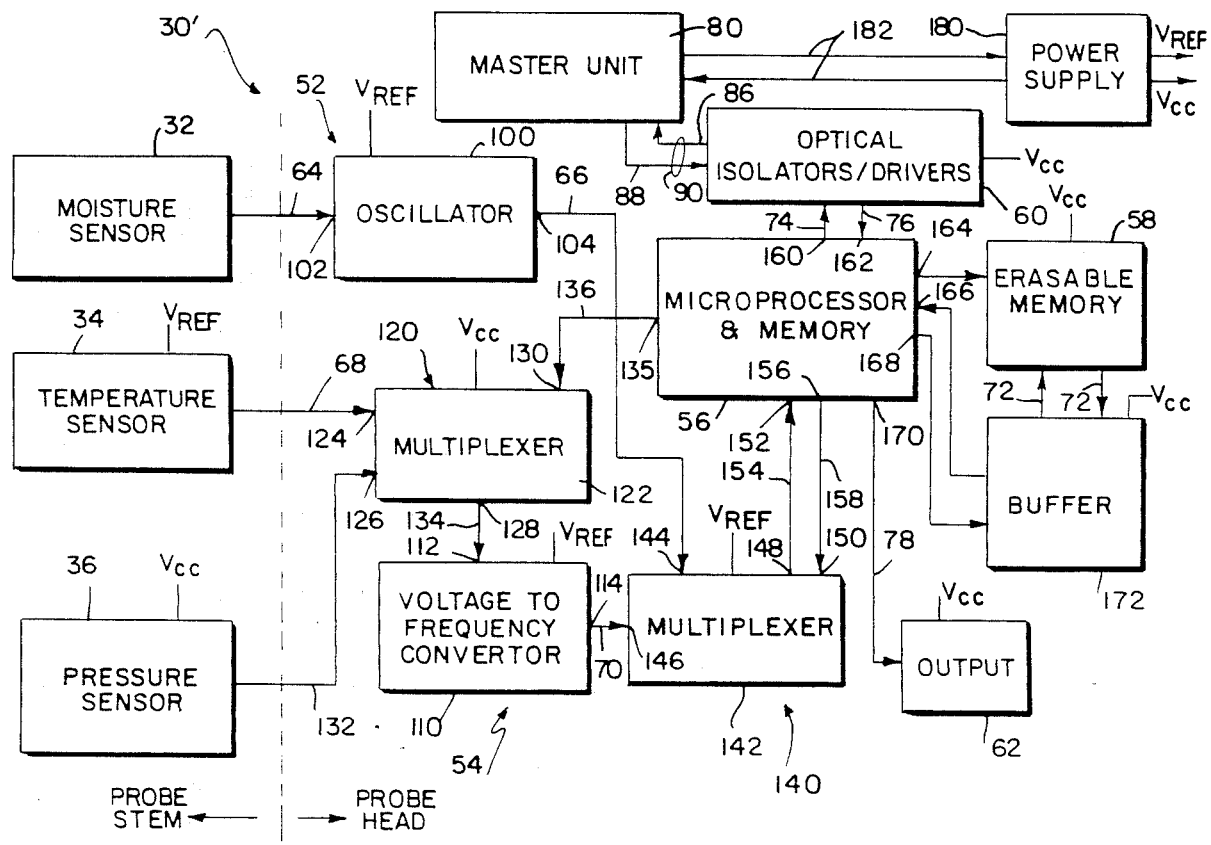
FIG. 4 is a functional block diagram of another embodiment of a sensing and signal-processing system included in the probe shown in FIG. 1.

A hygrometry probe 10 embodying the present invention is shown in FIG. 1. While for illustrative purposes the present invention is described as a probe for measuring the physical condition of moisture, temperature, and pressure, a probe embodying the invention could also be employed to measure different or additional physical conditions or parameters without departing from the scope of the invention.

In the illustrative embodiment, the hygrometry probe 10 includes a housing 12. Housing 12 has a head 14 providing a cavity 16 closed by a removable cover 18. Housing 12 further includes a hollow stem or blade 20 coupled to and extending outwardly from head 14. Probe 10 may be electrically coupled to an external monitoring system by data link 22. A sensing and signal-processing system 30 for sensing physical conditions or parameters and providing a linearized digital output is housed within the head 14 and stem 20 of the probe 10. Prove 10 is a stand-alone self-contained unit with the integrated capabilities of sensing physical conditions, linearizing the physical condition analog measurements, converting the analog measurements to digital signals, and transmitting serial data representing the measurements via a single line in the data line 22 to a master monitoring unit.

The sensing and signal-processing system 30 includes a moisture sensor 32, a temperature sensor 34, and a signal-processing circuit 50. In another embodiment, a sensing and signal-processing system 30' also includes a pressure sensor 36. The sensors 32, 34, and 36 are housed in the probe stem 20 and the signal-processing circuit 50 is housed in the probe head 14. It will be appreciated that hygrometry probe 10 may include only one sensor (e.g., a moisture sensor 32) without departing from the scope of the invention. The sensing and signal-processing system 30 shown in FIG. 3 includes the moisture sensor 32 and the temperature sensor 34.

The system 30' shown in FIG. 4 includes sensors 32 and 34 plus a pressure sensor 36.

While moisture sensor 32 may be any type of sensor for sensing moisture, in the preferred embodiment it is an aluminum-oxide capacitive sensor. Aluminum-oxide sensors are typically constructed in the manner shown in FIG. 2. An aluminum-oxide sensor senses moisture by measuring the change in impedance between two electrically conductive metal layers. The sensor 32 includes an electrically conductive aluminum base 40 and an aluminum-oxide (hygrometric) layer 42 on the base 40. A first electrode 44 contacts the base 40. A second electrically conductive layer 46 contacts the oxide layer 42 and provides a second electrode. Leads 48 electrically couple the sensor to the signal-processing circuit 50.

One illustrative embodiment of the sensing and signal-processing system 30 is shown in FIG. 3. The system 30 includes moisture sensor 32, moisture signal-conditioning circuit 52, temperature sensor 34, temperature signal-conditioning circuit 54, a signal processor 56 (e.g., microprocessor), an erasable memory device 58, optical coupler 60, and a digital output 62. Moisture sensor 32 is coupled to moisture signal-conditioning circuit 52 by an electrically conductive line 64. Moisture signal-conditioning circuit 52 is coupled to microprocessor 56 by an electrically conductive line 66. Temperature sensor 34 is coupled to temperature signal-conditioning circuit 54 by an electrically conductive line 68. Temperature signal-conditioning circuit 54 is coupled to microprocessor 22 by an electrically conductive line 70.

Microprocessor 56 is coupled to the erasable memory device 58 by multiple electrically conductive lines 72 providing bidirectional communication between the microprocessor 56 and the erasable memory 58. Microprocessor 56 is coupled to the optical coupler 60 by two electrically conductive lines 74 and 76. Line 76 provides an input to microprocessor 56, and line 76 provides an output to optical coupler 60. Microprocessor 56 is further coupled to output 62 by an electrically conductive line 78.

Probe 10 may be coupled to a master unit or monitoring system 80 by a single conductive data line 90. The monitoring system 80 may have a display 82 and a keyboard input 84. Data line 90 serves as both an input line 86 and an output line 88.

A more detailed embodiment of the sensing and signal-processing system 30' is shown in FIG. 4. In FIG. 4, the same reference numerals are used to identify elements identical to those shown in FIG. 3. Moisture signal-conditioning circuit 52 includes an oscillator 100 having an input 102 and an output 104. Input 102 is coupled to the moisture sensor 32 by the line 64. Moisture sensor 32 produces a voltage related to moisture. In response to this voltage, oscillator 100 generates a series of electrical pulses (square wave) having a frequency which varies in relationship to moisture. While oscillator 100 may be any conventional oscillator, in the preferred embodiment it is an LM556 dual timer manufactured by National Semiconductor Corporation.

Temperature signal-conditioning circuit 54 includes a voltage-to-frequency converter 110 having an input 112 and an output 114. In the embodiment of the sensing and signal-processing system 30 shown in FIG. 3, the input 112 of the voltage-to-frequency converter 110 is coupled to the temperature sensor 34 by the line 68. Temperature sensor 34 generates a DC voltage related to temperature. The voltage-to-frequency converter 110 converts the DC voltage generated by the temperature sensor 34 to a series of electrical pulses (square wave) having a frequency which varies in relationship to the DC voltage. In the preferred embodiment, temperature sensor 34 is an LM335 temperature sensor manufactured by National Semiconductor Corporation. The temperature sensor 34 includes a Zener diode (not shown) as the sensing element. In the preferred embodiment, the voltage-to-frequency converter is an LM331 converter manufactured by National Semiconductor Corporation.

In the embodiment of the sensing and signal-processing system 30 shown in FIG. 3, the outputs 104 and 114 of the oscillator 100 and voltage-to-frequency converter 110, respectively, are coupled directly to the microprocessor 56 by the lines 66 and 70, respectively.

The embodiment of the sensing and signal-processing system 30' shown in FIG. 4 includes pressure sensor 36. Pressure sensor 36 may be any conventional element for sensing pressure. In one embodiment, pressure sensor 36 is a bridge circuit. As shown in FIG. 4, temperature sensor 34 and pressure sensor 36 are coupled to the voltage-to-frequency converter 110 through a signal selection means 120. Signal selection means 120 is a multiplexer 122 having a first input 124 and a second input 126. Multiplexer 122 also includes an output 128 and a select input 130. The first input 124 is coupled to the temperature sensor 34 by the line 68. The second input 126 is coupled to the pressure sensor by an electrically conductive line 132. The output 128 of multiplexer 122 is coupled to the input 112 of the voltage-to-frequency converter 110 by an electrically conductive line 134. The select input 130 of the multiplexer 122 is coupled to a select output 135 of microprocessor 56 by an electrically conductive line 136. The multiplexer 122 selectively couples a temperature-related signal from temperature sensor 34 and a pressure-related signal from pressure sensor 36 to the voltage-to-frequency converter 110 in response to a select signal at input 130 produced by the microprocessor 56. In the preferred embodiment, multiplexer 122 is a CD4053 analog data multiplexer manufactured by National Semiconductor Corporation.

In sensing and signal-processing system 30', the oscillator 100 and voltage-to-frequency converter 110 are coupled to the microprocessor 56 by a second signal selection means 140. The second signal selection means 140 is a multiplexer 142. Multiplexer 142 has a first input 144, a second input 146, an output 148, and a signal-select input 150. The first input 144 is coupled to the output 104 of the oscillator 100 by the line 66. The second input 146 of multiplexer 142 is coupled to the output 114 of the voltage-to-frequency converter 110 by the line 70. The output 148 of the multiplexer 142 is coupled to an input 152 of the microprocessor 56 by an electrically conductive line 154. The select input 150 of the multiplexer is electrically coupled to a select output 156 of the microprocessor 156 by an electrically conductive line 158.

In the preferred embodiment, multiplexers 122 and 142 are portions of a single analog data multiplexer. Multiplexer 142 selectively couples the conditioned moisture-related signal provided by moisture sensor 32 and oscillator 100; the conditioned temperature-related signal provided by temperature sensor 34, multiplexer 122, and voltage-to-frequency converter 110; and the pressure-related signal provided by pressure sensor 36, multiplexer 122, and voltage-to-frequency converter 110 to the microprocessor 56 in response to a signal provided by microprocessor 56 at the select inputs 130 and 150 of multiplexers 122 and 142, respectively.

While various microprocessors could be used in the systems 30 and 30', in the preferred embodiment, microprocessor 56 is a 8748 microprocessor manufactured by Intel Corporation, having a memory for storing the operation program. In addition to having select outputs 135 and 156 and a signal input 152, the microprocessor 56 also includes a serial data output 160, a serial data input 162, and memory address 164 and data input/output lines 166 and 168, and a digital output 170. The serial data output 160 is coupled to the optical coupler 60 by the line 74. The serial data input 162 is coupled to the optical coupler 60 by the line 76. The erasable memory 58 is coupled to the microprocessor 56 by the memory address 164 and the data lines 166 and 168. The data input/output lines 166 and 168 are coupled to the erasable memory 58 through a buffer 172. The digital output 170 of microprocessor 56 is coupled to the output 62 by the line 78.

As in the embodiment of the sensing and signal-processing system 30 shown in FIG. 3, the sensing and signal-processing system 30' is coupled to the external master unit 80 through the single data transmission line 90.

In the preferred embodiment, the erasable memory 58 is a 2816 electronic erasable-programmable-read-only memory (EEPROM) manufactured by XICOR Corporation, the buffer 172 is a SN74LS373 manufactured by Texas Instruments Corporation, and the optical coupler 60 includes optical isolators/drivers of the type 4N37 manufactured by General Instrument Corporation.

The system 30' is driven by an internal power supply 180. Power supply 180 is coupled to the master monitoring unit 80 by electrically conductive lines 182. Lines 182 may also be included in the data link 22 from the probe 10. The power supply 180 produces a reference voltage $V_{REF}$ and a DC voltage $V_{CC}$ which are connected to the various circuit components of the system 30 or 30'.

In an illustrative embodiment, output 62 of microprocessor 56 may be coupled to a visual or audible indicator for indicating when the moisture, temperature, or pressure reach predetermined limits. The alarm may be provided as an integral part of the probe 10.

The erasable memory 58 provides means for programming and storing information in the system 30 or 30' which is peculiar to the moisture sensor 32 and the particular application for the probe 10. For each probe, the aluminum oxide sensor 32 will be different. Thus, the erasable memory 56 provides means for allowing the user to program the probe 10 with information peculiar to its moisture sensor 32. The erasable memory 56 also allows the user to store temporary information such as identification codes and alarm limits.

Figure 5:
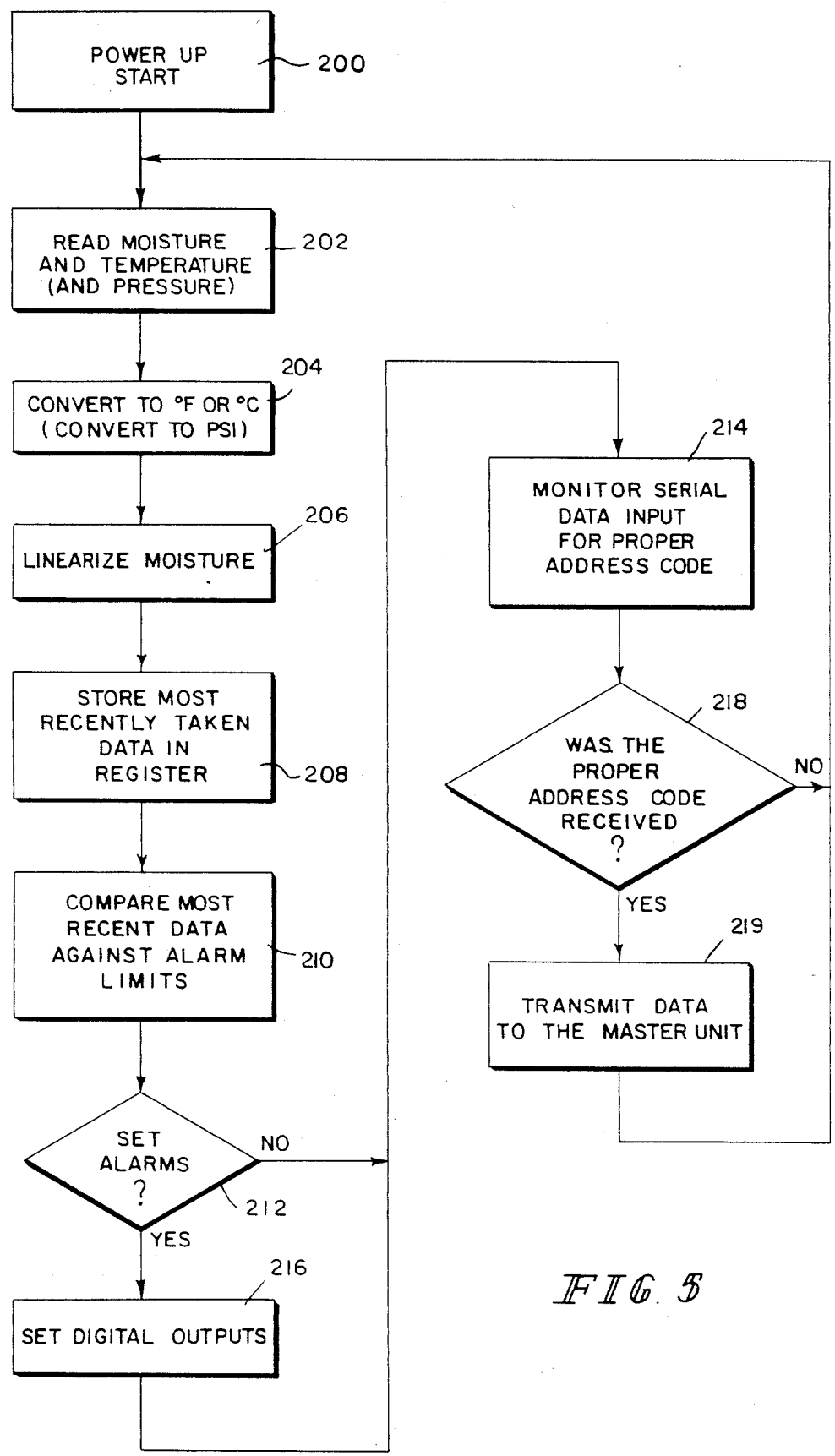
FIG. 5 is a flow diagram of the operational steps of the probe shown in FIG. 1.

The operation of systems 30 and 30' can best be described by referring to the system 30' shown in FIG. 4 and the flow diagram shown in FIG. 5. Microprocessor 56 has a system program in its memory for implementing the process steps shown in the flow diagram in FIG. 5. The programmable erasable memory 58 allows the user to program the microprocessor 56 with data and information peculiar to the moisture sensor 32 and the particular application of the probe 10.

The first step of the program executed by the microprocessor 56 is the power-up start sequence 200. After the microprocessor 56 finishes executing the power-up start sequence 200, it proceeds to step 202.

In step 202, the microprocessor reads the conditioned moisture-related signal, conditioned temperature-related signal, and the conditioned pressure-related signal. The microprocessor 56 achieves this step by setting select outputs 135 and 156 to selectively couple the conditioned signals from the moisture sensor 32, temperature sensor 34, and pressure sensor 36 to the microprocessor input 152. The microprocessor 56 will, by the state of the select outputs 135 and 156, know which condition-related signal is present at the signal input 152. The signal present at the signal input 152 will be a series of electrical pulses (generally a square wave), the frequency of which is related to the sensed condition. The microprocessor next proceeds to step 204.

In step 204, the microprocessor 56 converts the analog signal representative of the sensed condition to a digital value indictive of degrees Fahrenheit or Centigrade for temperature or psi for pressure. Those skilled in the art will recognize that these are standard units for indicating temperature and pressure. Once the microprocessor 56 converts the analog temperature-related signal and pressure-related signal to digital values, it proceeds to execute step 206.

In step 206, an algorithm programmed into the memory of the microprocessor 56 linearizes the digital value of the moisture-related signal. In the illustrative embodiment, this moisture-related signal represents the dew point. Another algorithm converts the dew point to second moisture-related signal which, in the illustrative embodiment, represents vapor pressure. The temperature value can be used to determine another moisture value as a function of the temperature. The pressure value can also be used to determine another moisture value as a function of the pressure. Thus, the microprocessor 56 converts the analog signals to digital value representative of the sensed moisture, temperature, and pressure, and the moisture linearization algorithm is employed to linearize the moisture-related signal and provide a digital moisture-related signal.

The moisture linearization algorithm makes use of a plurality of data points representative of dew point measurements empirically determined at different moisture levels with a preselected moisture sensor. Illustratively, five such data points are used, although the use of more than five data points would provide a higher degree of accuracy for the linearized value. The data points are stored in the memory of the microprocessor 56.

The slope-intercept equation for a straight line is stored in the memory of the microprocessor 56. This equation is $Y = MX + B$, where B is the value of the Y coordinate when the X coordinate is equal to 0 and M is the slope of the line. The microprocessor establishes straight-line segments between adjacent data points. The variable X is the value read from the moisture sensor 32. The microprocessor determines the two data points between which the moisture values X falls and determines the appropriate slope-intercept equation for calculating the dew point value. The microprocessor interpolates between the two data points by solving the slope-intercept equation for the Y value, dew point, using as the X value the reading from the moisture sensor 32.

After the moisture value has been linearized, the linearized moisture value (dew point) can be utilized by the microprocessor to calculate a variety of other moisture-related values. Illustratively, it is well known in the art that vapor pressure is logarithmically related to dew point. Therefore, the equivalent vapor pressure values for given dew point values can be pre-stored in a table in the memory of the microprocessor 56. The calculated dew point can then be used by the microprocessor as an index into the vapor pressure table to arrive at a vapor pressure value related to the calculated dew point value.

In another illustrative embodiment, the measured pressure value can be used by the microprocessor 56 in conjunction with the vapor pressure value determined as described previously, to arrive at the volumetric concentration of water in the environment being probed. The volume of water in parts-per-million is calculated by the microprocessor by dividing the vapor pressure value by the measured pressure value and multiplying the quotient by $10^6$.

In another illustrative embodiment, the concentration of water by weight in a hydrocarbon solution can be calculated by the microprocessor 56 utilizing a constant (K) stored in its memory, the vapor pressure value determined as discussed previously, and the measured temperature value. The constant K is the solubility of water in a particular hydrocarbon solution being probed. The constant K is pre-stored in the memory of the microprocessor 56. Additionally, the saturation vapor pressure at various temperatures are pre-stored in a table in the memory of the microprocessor 56.

The microprocessor 56 utilizes the measured temperature value as an index into the saturation vapor pressure table to select a value for the saturation vapor pressure for the hydrocarbon solution related to the temperature of the solution. The microprocessor 56 then divides the vapor pressure value by the selected saturation vapor pressure value and multiples the quotient by the constant K. The resulting value is the concentration of water by weight in the hydrocarbon solution being probed.

The algorithms just described are illustrative of the moisture-related parameters that can be determined by a probe embodying the present invention. However, the moisture-related parameters that can be determined by the invention are not to be limited to those described in the previously discussed algorithms.

In step 208, the digital moisture-related values, temperature value, and pressure value are stored in the memory of the microprocessor. In step 210, the microprocessor compares the stored digital values to alarm limits which have previously been programmed by the user into the erasable memory 58.

In step 212, the microprocessor determines on the basis of the comparison made in step 210 whether or not the alarms are to be set. If the alarms are not to be set, the microprocessor 56 proceeds to step 214. If the alarms are to be set, the microprocessor 56 will set its ditigal output 170 in step 216. As shown in FIG. 4, output 62 (representing the alarm output) is activated in response to the digital output 170 of microprocessor 56.

After executing step 216 or determining that the alarms are not to be set, the microprocessor 56 executes step 214. In step 214, the serial data input 162 is monitored by the microprocessor. The microprocessor 56 receives address codes from the master monitoring unit 80 and proceeds to step 218.

In step 218, the microprocessor 56 checks each address code which it receives at its serial data input 162 to determine if the address code is that of this particular microprocessor 56. If the address code is not that of the particular microprocessor 56, the microprocessor 56 returns to step 202 and begins executing the program sequence over again. If the address code is that of the microprocessor 56, it will then execute step 219.

In step 219, the microprocessor 56 transmits the values which it has stored for the sensed conditions to the master unit 80. After executing step 218, microprocessor 56 returns to step 202 and begins executing the program sequence over again.

The signal transmitted by the microprocessor 56 through the serial data output 160 is a serial string of binary digital data signals. The serial string of data signals may include a first digital moisture-related signal (dew point), a second digital moisture-related signal (vapor pressure), a digital temperature-related signal, and a digital pressure-related signal. Thus, a plurality of condition-related signals can be transmitted along a single data line 90 to the master unit 80.

It will be appreciated that additional condition sensors may be included in the probe 10. For example, as previously described, in addition to moisture and temperature sensors, the pressure sensor may also be included in probe 10. However, probe 10 and system 30' are not limited to moisture, temperature, and pressure sensors.

Figure 6:
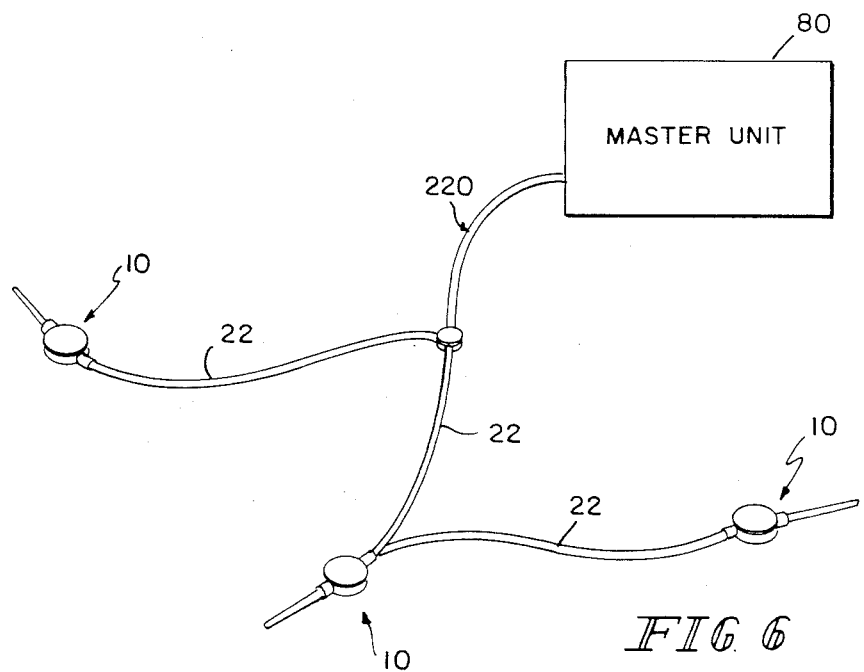
FIG. 6 is a diagrammatic view of a multiple probe system employing a plurality of probes constructed according to the present invention.

One of the advantages of a probe 10 which integrally includes sensors 32, 34, and 36 and the signal-processing circuit 50 and which provides a serial data output of digital signals representative of the measured conditions is that multiple probes 10 can be connected in a system with a single master unit 80. Such a multiple probe system is shown in FIG. 6. A plurality of probes 10 are shown coupled to the master unit 80 through a common data transmission line 220. As shown, the data transmission line 220 is common to each of the probes 10. Each probe 10 includes its own microprocessor 56 (see FIG. 4) which continuously monitors its serial data input 162 (see FIG. 4) to determine when its address code is received. Only when the microprocessor 56 in each probe 10 receives its address code does it transmit a digital signal via the common transmission line 220 to the master unit 80. Each probe 10 will have a different address code so that data from the probe is transmitted to the master unit 80 in a sequence controlled by the master unit 80.

It will be appreciated that various modifications may be made to the probe 10 without departing from the scope of the present invention. In particular, other signal-conditioning means and signal-selection means may be used. Further, other physical condition sensors may be used or added to the moisture, temperature, and pressure sensors described above.

What is claimed is:

1. A hygrometry probe comprising a housing, first sensing means in the housing for sensing moisture and providing a moisture-related signal, second sensing means in the housing for sensing a second physical condition and providing a second physical condition-related signal, signal-processing means in the housing for linearizing the moisture-related signal and providing a digital moisture-related signal and a digital second physical condition-related signal, the signal-processing means including means for generating a serial data output signal including the digital moisture-related signal and the digital second physical condition-related signal, and means for transmitting the serial data output signal to a central monitoring system along a single data transmission line.

2. The hygrometry probe of claim 1 wherein the second physical condition is temperature.

3. The hygrometry probe of claim 1 wherein the second physical condition is pressure.

4. The hygrometry probe of claim 1 wherein the signal-processing means further includes means for receiving an address signal from the central monitoring system and means for comparing the address signal to an address code of the signal-processing means to determine when to transmit the serial data output signal.

5. A probe for measuring physical conditions comprising a housing, first sensing means in the housing for sensing a first condition and providing a first signal related to the first condition, second sensing means in the housing for sensing a second condition and providing a second signal related to the second condition, signal-processing means in the housing for processing the first signal as a function of the second signal and providing a third signal related to the first condition, the signal-processing means including means for generating a serial data output signal including data from the first signal, second signal, and third signal.

6. A hygrometry probe comprising a housing, first sensing means in the housing for sensing moisture and providing a first moisture-related signal, second sensing means in the housing for sensing temperature and providing a temperature-related signal, signal-processing means in the housing for processing the first moisture-related signal as a function of the temperature-related signal and providing a second moisture-related signal, the signal-processing means including means for generating a serial digital output signal including a digital first moisture-related signal, a digital temperature-related signal, and a digital second moisture-related signal.

7. The hygrometry probe of claim 6 further comprising a first signal-conditioning means coupling the first sensing means to the signal-processing means and second signal-conditioning means coupling the second sensing means to the signal-processing means.

8. The hygrometry probe of claim 7 wherein the first signal-conditioning means includes means providing a series of electrical pulses having a frequency related to moisture and the second signal-conditioning means includes means for converting a voltage to a series of electrical pulses having a frequency related to temperature.

9. The hygrometry probe of claim 8 further comprising a third sensing means in the housing for sensing pressure and providing a pressure-related signal and signal-selection means coupling the second sensing means and the third sensing means to the second signal-conditioning means, the signal-processing means further processes the first moisture-related signal as a function of the pressure-related signal and provides a third moisture-related signal, and the generating means generates the serial digital data signal which further includes a digital pressure-related signal and a digital third moisture-related signal.

10. The hygrometry probe of claim 9 further comprising signal-selection means coupling the first signal-conditioning means and the second signal-conditioning means to the signal-processing means.

11. The hygrometry probe of claim 10 wherein the first moisture-related signal is a dew point.

12. The hygrometry probe of claim 6 wherein the housing includes a head and a hollow stem, the first and second sensing means are housed in the stem, and the signal-processing means is housed in the head.

13. The hygrometry probe of claim 12 further comprising a third sensing means housed in the stem for sensing pressure and providing a pressure-related signal and means for coupling the third sensing means to the signal-processing means, the signal-processing means processes the first moisture-related signal as a function of the pressure-related signal to provide a third moisture-related signal, and the generating means generates the serial digital data signal which further includes a digital pressure-related signal and a digital third moisture-related signal.

14. An apparatus for measuring at least two physical conditions, the apparatus comprising means for sensing a first condition and generating a first signal, means for sensing a second condition and generating a second signal, signal-processing means for linearizing the first signal and converting the first and second signals to digital output signals indicative of the first and second conditions, and means for transmitting the digital output signals in series to a central monitoring system along a single transmission line.

15. An apparatus for measuring moisture and temperature and linearizing the moisture measurement comprising a probe having a head providing a first compartment and a stem providing a second compartment, means in the second compartment for sensing moisture and providing a moisture-related signal, means in the second compartment for sensing temperature and providing a temperature-related signal, means in the first compartment for linearizing the moisture-related signal and converting the moisture-related signal and temperature-related signal to digital signals indicative of moisture and temperature, and means for transmitting the digital signals from the probe to a monitoring system along a single data transmission line.

16. The apparatus of claim 15 further comprising programmable means in the second compartment for storing information related to the moisture-sensing means and bidirectional means for coupling the programmable means to the signal-processing means.

17. A hygometry probe comprising a housing, first sensing means in the housing for sensing moisture and providing a moisture-related signal, second sensing means in the housing for sensing temperature and providing a temperature-related signal, third sensing means in the housing for sensing pressure and providing a pressure-related signal, and signal-processing means in the housing for linearizing the moisture-related signal and providing a digital moisture-related signal, a digital temperature-related signal, and a digital pressure-related signal.

18. The hygometry probe of claim 17 wherein the signal-processing means further includes means for generating a serial data output signal which includes the digital moisture-related signal, the digital temperature-related signal, and the digital pressure-related signal, and means for transmitting the serial data output signal to a central monitoring system along a single data transmission line.

19. A hygometry probe comprising a housing, first sensing means in the housing for sensing moisture and providing a first moisture-related signal, second sensing means in the housing for sensing pressure and providing a pressure-related signal, and signal-processing means in the housing for processing the first moisture-related signal as a function of the pressure-related signal and providing a second moisture-related signal, the signal-processing means including means for generating a serial digital output signal including a digital first moisture-related signal, a digital pressure-related signal, and a digital second moisture-related signal.

20. A hygometry probe comprising a housing, first sensing means in the housing for sensing moisture and providing a moisture-related signal, second sensing means in the housing for sensing pressure and providing a pressure-related signal, and signal-processing means in the housing for linearizing the moisture-related signal and providing a digital moisture-related signal and a digital pressure-related signal.

21. A hygometry probe comprising a housing, first sensing means in the housing for sensing moisture and providing a moisture-related signal, second sensing means in the housing for sensing temperature and providing a temperature-related signal, and signal-processing means in the housing for linearizing the moisture-related signal and providing a digital moisture-related signal and a digital temperature-related signal.

* * * * *